United States Patent
Lee et al.

(10) Patent No.: US 6,815,094 B2
(45) Date of Patent: Nov. 9, 2004

(54) DIPHENYL ANTHRACENE DERIVATIVES AND ORGANIC ELECTROLUMINESCENT DEVICE EMPLOYING THE SAME

(75) Inventors: Ji-hoon Lee, Chungcheongbuk-do (KR); Soo-hyoung Lee, Gyeonggi-do (KR); Jhun-mo Son, Gyeonggi-do (KR)

(73) Assignee: Samsung SDI Co., Ltd., Gyeonggi-do (KR)

( * ) Notice: Subject to any disclaimer, the term of this patent is extended or adjusted under 35 U.S.C. 154(b) by 0 days.

(21) Appl. No.: 10/749,390

(22) Filed: Jan. 2, 2004

(65) Prior Publication Data

US 2004/0146746 A1 Jul. 29, 2004

(30) Foreign Application Priority Data

Jan. 2, 2003 (KR) .................. 10-2003-0000049

(51) Int. Cl.⁷ .................. H05B 33/14; C09K 11/06
(52) U.S. Cl. .................. 428/690; 428/917; 313/504; 257/103; 564/305; 548/440; 544/102; 544/35; 252/301.16
(58) Field of Search .................. 428/690, 917; 313/504; 257/103; 564/305; 548/440; 544/35, 102; 252/301.16

(56) References Cited

U.S. PATENT DOCUMENTS

2004/0082756 A1 * 4/2004 Sezi et al. .................. 528/363

* cited by examiner

*Primary Examiner*—Dawn Garrett
(74) *Attorney, Agent, or Firm*—Lee & Sterba, P.C.

(57) ABSTRACT

A blue electroluminescent compound and an organic electroluminescent device using the blue electroluminescent compound, which includes a 9,10-diphenyl anthracene unit in its backbone and has alkoxy groups and substituted or unsubstituted amino group introduced to the 2 and 5 positions on the phenyl group in the diphenyl anthracene unit.

10 Claims, 10 Drawing Sheets

DIPHENYL ANTHRACENE DERIVATIVES AND ORGANIC ELECTROLUMINESCENT DEVICE EMPLOYING THE SAME

BACKGROUND OF THE INVENTION

1. Field of the Invention

Embodiments of the present invention relate to diphenyl anthracene derivatives, and to an organic electroluminescent device using the same. More particularly, embodiments of the invention relate to diphenyl anthracene derivatives that are useful as blue electroluminescent compounds, and to an organic electroluminescent device using the same that offers improved efficiency, driving voltage and luminance.

2. Description of the Related Art

An organic electroluminescent (organic EL) device is an active drive type emission display device that operates under the principle that when current is applied to fluorescent or phosphorescent organic compound layers (hereinafter "organic layers"), electrons and holes are combined in the organic layers to then electroluminesce. Organic electroluminescent devices have various advantages including being lightweight, simple components, having a simplified fabrication process, and offering a wide range of colors with high luminescence. Also, organic EL devices can enable moving picture display perfectly with high color purity, and the devices have electrical properties suitable for portable electronic devices at low power consumption and low driving voltage.

Such organic EL devices typically can be classified into low molecular weight organic EL devices and polymer EL devices, depending on the materials used to manufacture the devices.

Low molecular weight organic EL devices have advantages, including being simple and easy to synthesize and purify to a high degree of emissive compounds, and three primary color pixels can easily be obtained. However, since organic layers typically are formed by vacuum deposition, low molecular weight organic EL devices are difficult to be suitably applied for large-screen size processes, which typically use a spin coating method or an ink jet printing method. Therefore, in order to apply the low molecular weight organic EL devices for practical applications, there is still room for improvement in quantum efficiency and color purity, and there remains a need to prevent crystallization of thin layers.

In order for low molecular weight organic EL devices to exhibit high-efficiency, high-luminance emission properties, they typically must have a multiple-layered structure of organic layers, including a hole injection layer, a hole transporting layer, an electron transporting layer, a hole blocking layer, etc. Such organic layers should be stable thermally and electrically during operation of the device because when a voltage is applied, thermally unstable molecules having low morphological stability are rearranged due to heat generated at the device, resulting in local crystallization and lowering of emission efficiency, thereby shortening the useful life of the device.

Research on polymer EL devices has been accelerated since the discovery of the ability of poly(1,4-phenylene vinylene) (PPV), π-conjugated polymer, to emit light when exposed to electricity. π-conjugated polymers have an alternating structure of single bonds (σ-bonds) and double bonds (π-bonds), where π-electrons are evenly distributed to be freely movable in the polymer chain. Accordingly, π-conjugated polymers have semiconducting properties and can emit light of a visible range corresponding to the HOMO (highest occupied molecular orbital)-LUMO (lowest unoccupied molecular orbital) energy bandgap, via proper molecular designing, when applied to an emissive layer of an EL device. Such a polymer can be formed as a thin layer by spin coating or printing during the manufacture of EL devices, so that the EL device can be fabricated in a simplified manner and can easily be used in making a large-screen size at low costs. However, such polymer EL devices have lower emission efficiency than low molecular weight EL devices, and they experience shortened lifetime characteristics due to deterioration of emissive polymer. Since defects that promote deterioration in molecular chains are generated during synthesis of such polymer materials, and impurities are difficult to refine, it is difficult to obtain high-purity materials.

To address the problems of polymer EL devices while having advantages of both polymers and low molecular weight materials, there is demand for development of new materials.

The description herein of various disadvantages associated with known materials, methods, and apparatus is in no way intended to limit the various embodiments of the invention. Indeed, certain embodiments of the invention may include one or more known materials, methods, apparatus, without suffering from the disadvantages described herein.

SUMMARY OF THE INVENTION

Various embodiments of the present invention provide diphenyl anthracene derivatives free of molecular defects, having improved thermal stability and crystal stability, that are easily purified, and easily capable of forming a thin layer using a soluble solvent. Embodiments of the present invention also provide an organic EL device with improved luminance, driving voltage and emission efficiency by employing the diphenyl anthracene derivatives.

In accordance with a feature of an embodiment of the present invention, there is provided a diphenyl anthracene derivative represented by the following formula:

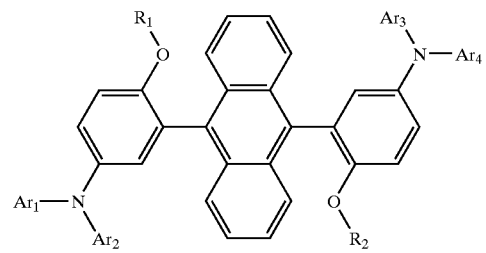

wherein $R_1$ and $R_2$ are independently a hydrogen atom; a $C_{1-20}$ linear or branched alkyl group; a $C_{5-20}$ cycloalkyl group; a $C_{6-20}$ aryl group; a $C_{4-20}$ heteroaryl group; or a $C_{6-20}$ aryl group having at least one substituent selected from the group consisting of a halogen atom, a $C_{1-10}$ halogenated alkyl group, —Si(R)(R')(R''), a $C_{1-10}$ alkyl group, a $C_{1-10}$ alkoxy group, a $C_{6-10}$ aryl group, a $C_{4-10}$ heteroaryl group and —N(R)(R'), $Ar_1$, $Ar_2$, $Ar_3$ and $Ar_4$ are independently a hydrogen atom; a $C_{1-20}$ linear or branched alkyl group; a $C_{5-20}$ cycloalkyl group; a $C_{6-20}$ aryl group; a $C_{4-20}$ heteroaryl group; or a $C_{6-20}$ aryl group having at least one substituent group selected from the group consisting of a halogen atom, a $C_{1-10}$ halogenated alkyl group, —Si(R)(R')(R"), a $C_{1-10}$ alkyl group, a $C_{1-10}$ alkoxy group, a $C_{6-10}$ aryl group, a $C_{4-10}$ heteroaryl group and —N(R)(R'), where at least one selected from the group consisting of $Ar_1$ and $Ar_2$, and $Ar_3$ and $Ar_4$ can be interconnected, respectively, and R, R' and R" are independently selected from the group consisting of a hydrogen atom, a $C_{1-10}$ alkyl group, a $C_{1-10}$ alkoxy group, a $C_{6-10}$ aryl group and a $C_{4-10}$ heteroaryl group.

In accordance with another feature of an embodiment of the present invention, there is provided an organic EL device comprising an organic layer positioned between a pair of electrodes, the organic layer containing the above-mentioned diphenyl anthracene derivative.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

Figure 1A:
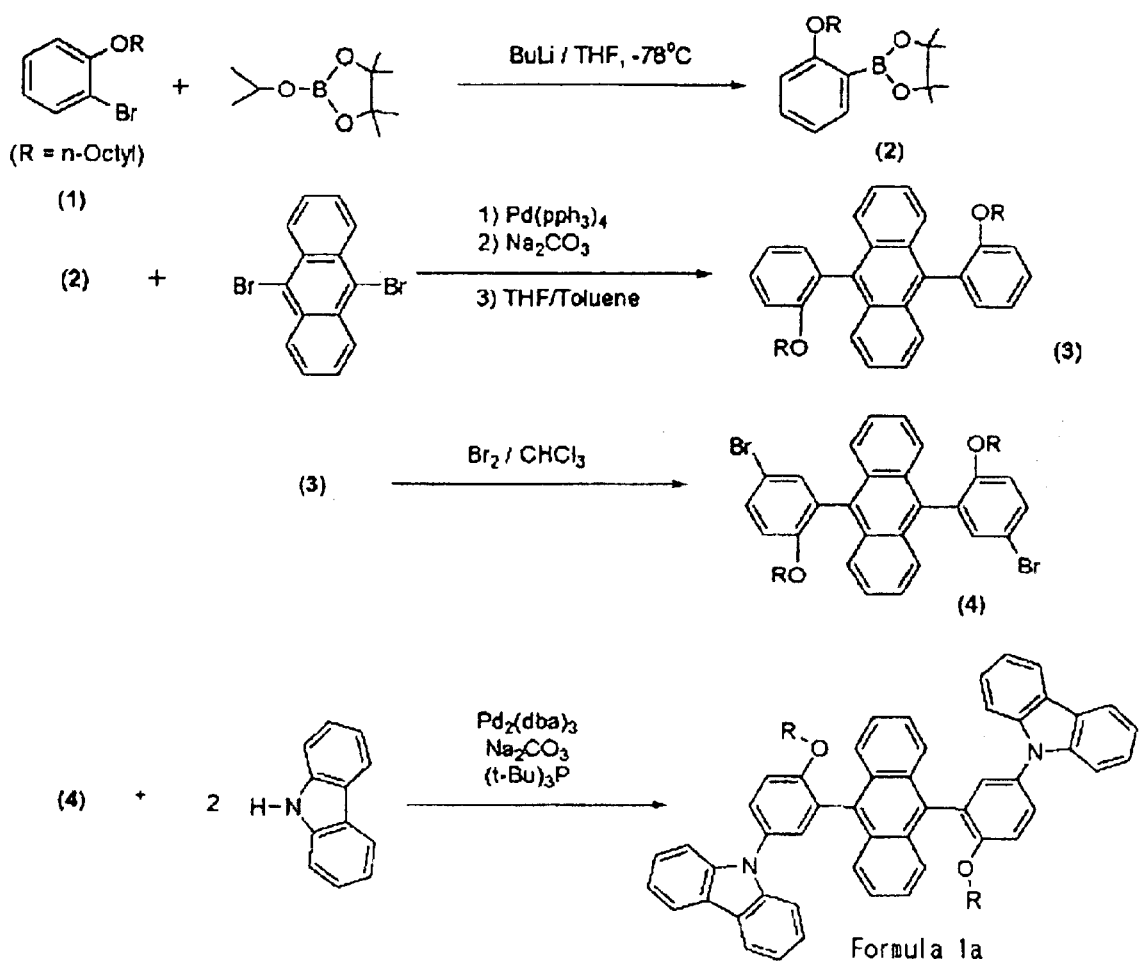
FIG. 1A is a reaction scheme illustrating the synthesis of a compound represented by formula 1a according to Synthesis Example 1 herein.

Korean Priority Application No. 2003-49, filed on Jan. 2, 2003, is incorporated herein in its entirety by reference. The present invention will be described in detail below.

A diphenyl anthracene derivative represented by formula 1 according to preferred embodiments of the present invention exhibits a blue electroluminescent property. The diphenyl anthracene derivative preferably has a 9,10-diphenyl anthracene unit in its backbone and alkoxy groups and substituted or unsubstituted amino groups introduced to the 2 and 5 positions of the phenyl in the diphenyl anthracene unit. Several disadvantages of the low molecular weight/polymer materials can be overcome by such a structural characteristic of the diphenyl anthracene derivative represented by formula 1. In addition, several advantages of the low molecular weight/polymer materials can be realized by use of the diphenyl anthracene derivative represented by formula 1. That is, the materials can be free of molecular defects, easily purified, and easily capable of forming a thin layer using a soluble solvent.

The compound represented by formula 1 preferably has a twist structure of diphenyl anthracene having an alkoxy group so that the band gap between HOMO and LUMO is advantageously wide. A substituted or unsubstituted amino group having good hole transporting capability is introduced to a para-position of an alkoxy group, thereby improving charge transporting capability. Thus, an organic EL device having good luminance and driving voltage characteristics can be manufactured by using the diphenyl anthracene derivative represented by formula 1 as a light-emitting material alone or in combination with a general dopant. The diphenyl anthracene derivative represented by formula 1 can be used as one of the materials of a hole injection layer or a hole transport layer as well as in an emissive layer.

The diphenyl anthracene derivative of formula 1 preferably is:

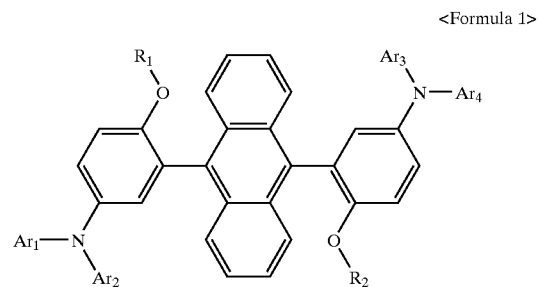

<Formula 1> wherein: $R_1$ and $R_2$ are independently a hydrogen atom; a $C_{1-20}$ linear or branched alkyl group; a $C_{5-20}$ cycloalkyl group; a $C_{6-20}$ aryl group; a $C_{4-20}$ hetroaryl group; or a $C_{6-20}$ aryl group having at least one substituent selected from the group consisting of a halogen atom, a $C_{1-10}$ halogenated alkyl group, —Si(R)(R')(R"), a $C_{1-10}$ alkyl group, a $C_{1-10}$ alkoxy group, a $C_{6-10}$ aryl group, a $C_{4-10}$ heteroaryl group and —N(R)(R');

$Ar_1$, $Ar_2$, $Ar_3$ and $Ar_4$ are independently a hydrogen atom; a $C_{1-20}$ linear or branched alkyl group; a $C_{5-20}$ cycloalkyl group; a $C_{6-20}$ aryl group; a $C_{4-20}$ hetroaryl group; or a $C_{6-20}$ aryl group having at least one substituent group selected from the group consisting of a halogen atom, a $C_{1-10}$ halogenated alkyl group, —Si(R)(R')(R"), a $C_{1-10}$ alkyl group, a $C_{1-10}$ alkoxy group, a $C_{6-10}$ aryl group, a $C_{4-10}$ heteroaryl group and —N(R)(R'), where at least one selected from the group consisting of $Ar_1$ and $Ar_2$, and $Ar_3$ and $Ar_4$ can be interconnected, respectively; and R, R' and R" are independently selected from the group consisting of a hydrogen atom, a $C_{1-10}$ alkyl group, a $C_{1-10}$ alkoxy group, a $C_{6-10}$ aryl group and a $C_{4-10}$ heteroaryl group.

In formula 1, —N($Ar_1$)($Ar_2$) and —N($Ar_3$)($Ar_4$) preferably are independently a group represented by formula 2 or 3, and more preferably a carbazole derivative group represented by formula 3:

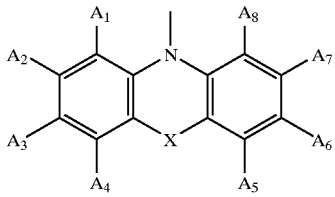
<Formula 2>

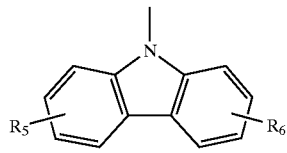
<Formula 3> wherein: X is —$(CH_2)_n$—, where n is an integer of 0~2, —$C(R_3)(R_4)$—, —CH=CH—, —S—, —O— or —$Si(R_3)(R_4)$—;

$A_1$, $A_2$, $A_3$, $A_4$, $A_5$, $A_6$, $A_7$, $A_8$, $R_3$, $R_4$, $R_5$ and $R_6$ are independently a hydrogen atom; a $C_{1-20}$ linear or branched alkyl group; a $C_{5-20}$ cycloalkyl group; a $C_{6-20}$ aryl group; a $C_{4-20}$ hetroaryl group; or a $C_{6-20}$ aryl group having at least one substituent selected from the group consisting of a halogen atom, a $C_{1-10}$ halogenated alkyl group, —Si(R)(R')(R''), a $C_{1-10}$ alkyl group, a $C_{1-10}$ alkoxy group, a $C_{6-10}$ aryl group, a $C_{4-10}$ heteroaryl group and —N(R)(R');

at least one selected from the group consisting of $A_1$ and $A_2$, $A_2$ and $A_3$, $A_3$ and $A_4$, $A_5$ and $A_6$, $A_6$ and $A_7$, and $A_7$ and $A_8$ can be interconnected, respectively; and R, R' and R'' are independently selected from the group consisting of a hydrogen atom, a $C_{1-10}$ alkyl group, a $C_{1-10}$ alkoxy group, a $C_{6-10}$ aryl group and a $C_{4-10}$ heteroaryl group.

Examples of the group represented by formula 2 include groups (2a)–(2h):

(2a)
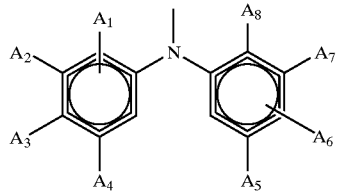

(2b)
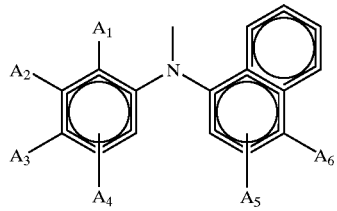

(2c)
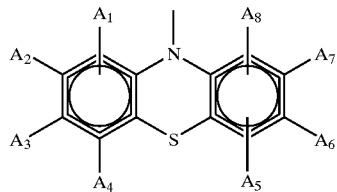

(2d)
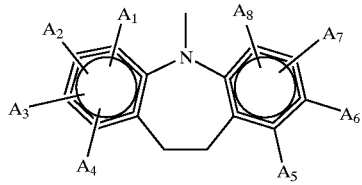

(2e)
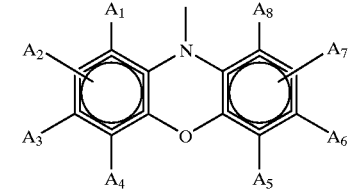

(2f)
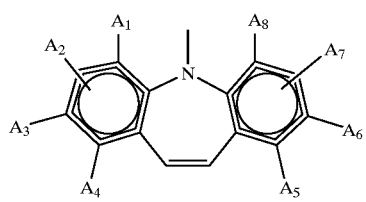

(2g)
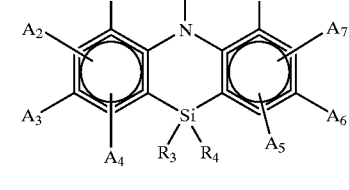

(2h)
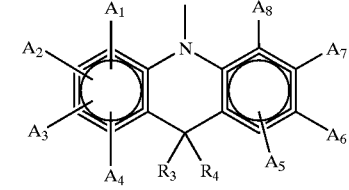

wherein $A_1$, $A_2$, $A_3$, $A_4$, $A_5$, $A_6$, $A_7$, $A_8$, $R_3$ and $R_4$ are as defined as above.

In formula 3, $R_5$ and $R_6$ are preferably a group represented by formula 4:

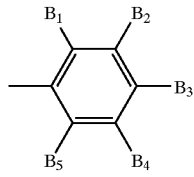
<Formula 4> wherein $B_1$, $B_2$, $B_3$, $B_4$ and $B_5$ are independently a hydrogen atom; a $C_{1-20}$ linear or branched alkyl group; a $C_{5-20}$ cycloalkyl group; a $C_{6-20}$ aryl group; a $C_{4-20}$ hetroaryl group; or a $C_{6-20}$ aryl group having at least one substituent selected from the group consisting of a halogen atom, a $C_{1-10}$ halogenated alkyl group, —Si(R)(R')(R''), a $C_{1-10}$ alkyl group, a $C_{1-10}$ alkoxy group, a $C_{6-10}$ aryl group, a $C_{4-10}$ heteroaryl group and —N(R)(R'), and R, R' and R'' are independently selected from the group consisting of a hydrogen atom, a $C_{1-10}$ alkyl group, a $C_{1-10}$ alkoxy group, a $C_{6-10}$ aryl group and a $C_{4-10}$ heteroaryl group.

A diphenyl derivative represented by formula 1 is preferably a compound represented by formula 1a, 1b or 1c:

<Formula 1a>

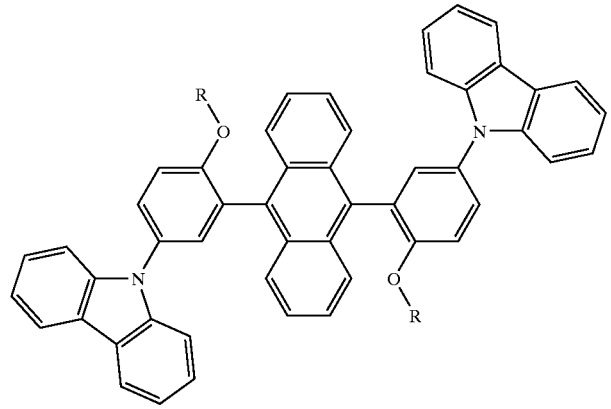

<Formula 1b>

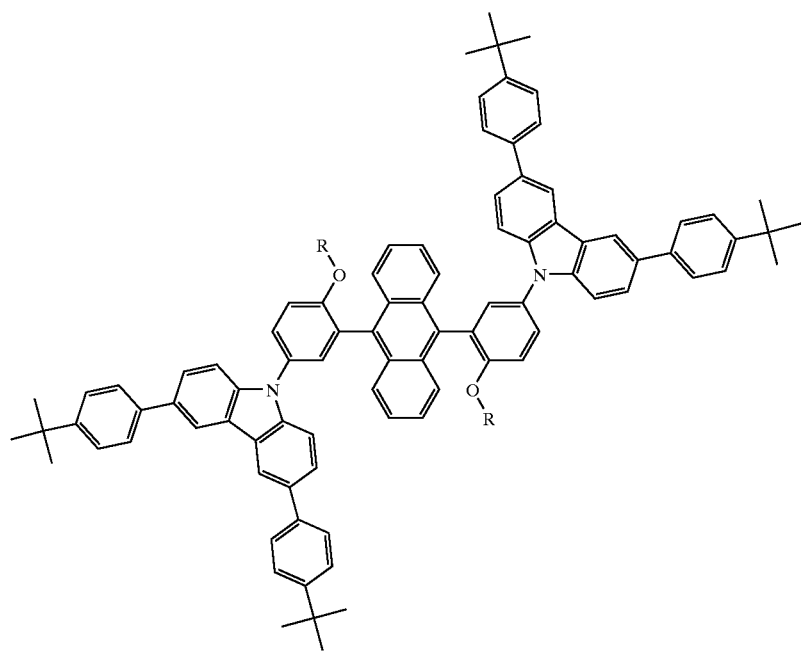

<Formula 1c>

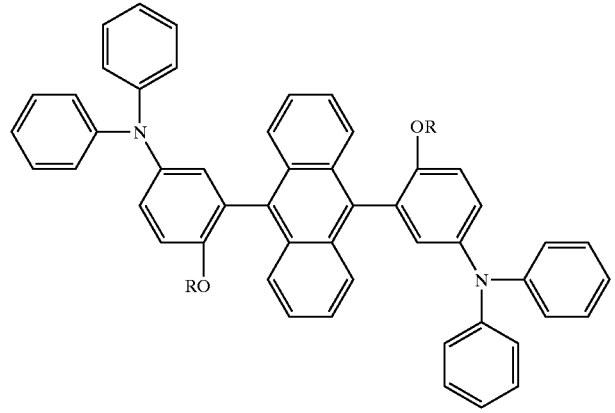

wherein R is a $C_{1-20}$ linear or branched alkyl group.

An organic electroluminescent (EL) device employing the diphenyl anthracene derivative represented by formula 1 according to preferred embodiments of the present invention and a manufacturing method thereof now will be described.

FIGS. 2A through 2F are views schematically illustrating laminated structures of organic electroluminescent (EL) devices manufactured in accordance with the examples of the present invention.

Figure 2A:
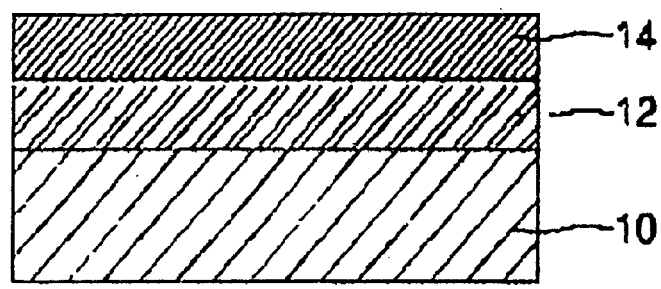
FIGS. 2A through 2F are views schematically illustrating laminated structures of organic electroluminescent (EL) devices manufactured in accordance with the examples herein.
Figure 2B:
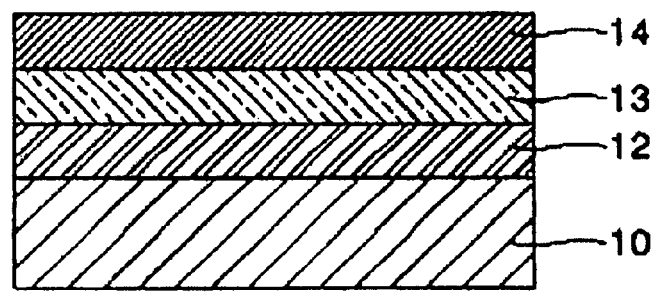

Referring to FIG. 2A, an emissive layer 12 having the diphenyl anthracene derivative represented by formula 1 preferably is laminated on a first electrode 10 and a second electrode 14 then preferably is formed on the emissive layer 12. Referring to FIG. 2B, a hole blocking layer (HBL) 13 can be laminated on the emissive layer 12 having the diphenyl anthracene derivative represented by formula 1 laminated on the first electrode 10, and the second electrode 14 formed on the HBL 13.

Figure 2C:
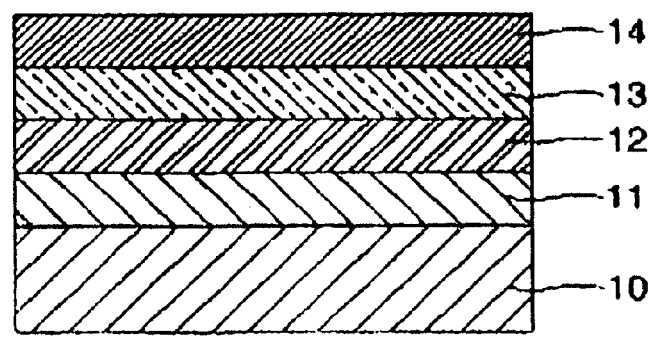
Figure 2D:
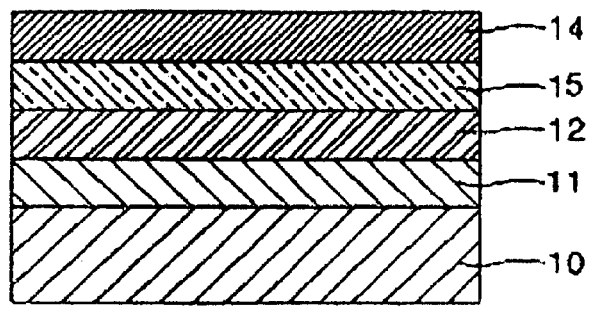

Referring to FIG. 2C, a hole injection layer (HIL) 11 preferably is formed between the first electrode 10 and the emissive layer 12. The organic EL device shown in FIG. 2D has the same laminated structure as that shown in FIG. 2C except that an electron transport layer (ETL) 15, instead of the HBL 13, is formed on the emissive layer 12. The organic EL device shown in FIG. 2E has the same laminated structure as that shown in FIG. 2C except that a dual layer having a HBL 13 and an ETL 15 sequentially laminated, instead of the HBL 13, is formed on the emissive layer 12 having the diphenyl anthracene derivative represented by formula 1. In some cases, an electron injection layer may be further formed between the ETL 15 and the second electrode 14.

Figure 2E:
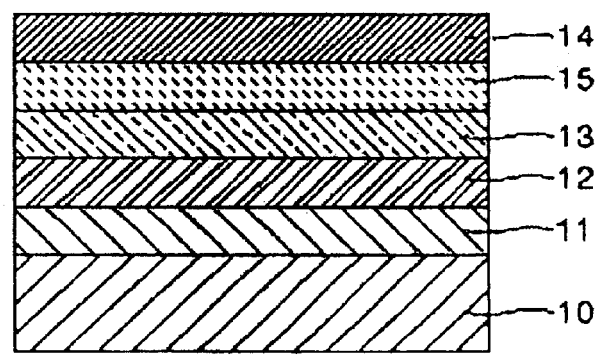
Figure 2F:
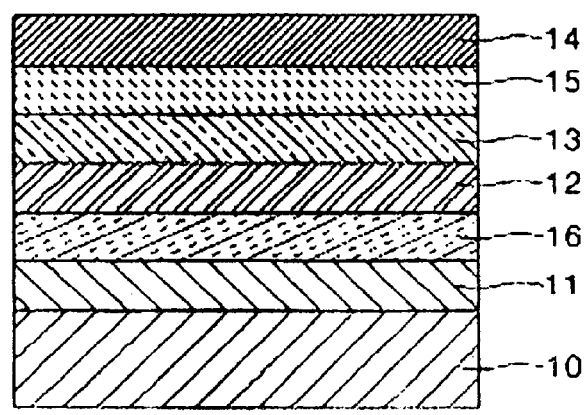

The organic EL device shown in FIG. 2F has the same laminated structure as that shown in FIG. 2E except that a hole transport layer (HTL) 16 is further formed between the HIL 11 and the emissive layer 12. Here, the HTL 16 serves to prevent impurities from infiltrating from the HIL 11 to the emissive layer 12.

The organic EL device according to the present invention can be manufactured by, but not limited to, conventional methods. Using the guidelines provided herein, those skilled in the art will be capable of manufacturing an organic EL device. A method of manufacturing an organic EL device according to a preferred embodiment of the present invention now will be described.

A first electrode 10 preferably is patterned on a substrate (not shown). The substrate can be any substrate used in a conventional organic EL device, preferably a glass substrate that is transparent and has surface smoothness, manageability and waterproofness, or a transparent plastic substrate. Examples of suitable substrate materials for use in embodiments of the invention include a glass substrate, a polyethyleneterephthalate substrate, a polycarbonate substrate and polyimide substrate. The substrate preferably has a thickness of 0.3 to 1.1 mm.

Any material commonly used in the field can be used to form the first electrode 10. In the case where the first electrode 10 is a cathode, the cathode preferably is made of a conductive metal capable of easily injecting holes or an oxide thereof. Preferred materials for the first electrode 10 include, but are not limited to, ITO (Indium Tin Oxide), IZO (Indium Zinc Oxide), nickel (Ni), platinum (Pt), gold (Au) and iridium (Ir).

The substrate having the first electrode 10 preferably is cleaned and UV/O$_3$ treatment then performed. It is preferred to use an organic solvent such as isopropanol (IPA) or acetone to clean the substrate.

A hole injection layer 11 preferably is selectively formed on the first electrode 10 of the cleaned substrate. Forming the hole injection layer 11 in such a manner increases the contact resistance between the first electrode 10 and the emissive layer 12, and improves the hole transporting capability of the first electrode 10 with respect to the emissive layer 12, thereby improving the driving voltage and lifetime characteristic of the device. Any material commonly used in the field can be suitably employed for the hole injection layer 11. Preferred materials for the hole injection layer 11 include, but are not limited to, PEDOT {poly(3,4-ethylenedioxythiophene)}/PSS(polystyrene parasulfonate), starburst materials, copper phthalocyanine, polythiophene, polyaniline, polyacetylene, polypyrrole, polyphenylene vinylene, or derivatives of these compounds, and m-MTDATA (4,4',4"-tris[N-(3-methylphenyl)—N-phenylamino]triphenylamine). The hole injection layer 11 can be spin-coated on the first electrode 10 and dried, thereby forming a hole injection layer 11. The hole injection layer 11 preferably has a thickness of from about 300 to about 2000 Å, more preferably from about 500 to about 1100 Å. If the thickness of the hole injection layer 11 is not within the range specified above, hole injection capability is undesirably poor. The drying preferably is performed at a temperature within the range of from about 100 to about 250° C.

The emissive layer 12 preferably is formed by spin-coating an emissive layer forming composition on the hole injection layer 11 and drying. The emissive layer forming composition typically comprises 0.5 to 5% by weight of diphenyl anthracene derivative represented by formula 1 as an emissive material and 99.5 to 95% by weight of a solvent, although any suitable amount can be used. Those skilled in the art are capable of determining a suitable amount of diphenyl anthracene derivative to be used in various embodiments of the invention. Any material that can dissolve the emissive material can be used as the solvent, and suitable examples thereof include toluene and chlorobenzene.

In some cases, the composition used to form the emissive layer may be mixed with a light-emitting material to then be used as an emissive layer. The amount of the light-emitting material varies, and preferably is within the range of from about 99.9 to about 0.1% by weight, based on from about 0.1 to about 99.9% by weight of the diphenyl anthracene derivative represented by formula 1. Any material can be used to form the emissive layer, including, but not limited to, polyarylenes, poly(p-phenylenes), poly(p-phenylene vinylenes), or polyfluorenes, and examples thereof include poly(9,9-dioctylfluorene) (PC8F), poly(spirofluorenes) and 2-Methyloxy-5-(2-ethylhexyloxy)-p-phenylene vinylene (MEHPPV).

Preferably, the thickness of the emissive layer 12 can be is adjusted to be within the range of from about 100 to about 1000 Å, more preferably from about 500 to about 1000 Å, by adjusting the concentration of the emissive layer forming composition and the spin speed during spin coating. If the thickness of the emissive layer 12 is less than about 100 Å, emission efficiency may be lowered. If the thickness of the emissive layer 12 is greater than 1000 Å, the driving voltage may undesirably increase. Skilled artisans are capable of varying the thickness of the emissive layer 12 to be within a desirable range.

A hole transport layer 16 may be selectively formed between the hole injection layer 11 and the emissive layer 12. Any material having hole transporting capability can be used, and examples thereof include PEDOT, polyaniline and polytriphenylamine. The thickness of the hole transport layer preferably is within the range of from about 100 to about 1000 Å.

A hole blocking layer 13 and/or an electron transport layer 15 may be formed on the emissive layer 12 by evaporation or spin coating. The hole blocking layer 13 is believed to prevent excitons formed from an emissive material from migrating to the electron transport layer 15, or to prevent holes from migrating to the electron transport layer 15.

Examples of materials suitable for use in forming the hole blocking layer 13 include TAZ (3-phenyl-4-(1'-naphthyl)

-5-phenyl-1,2,4-triazole), BCP (2,9-dimethyl-4,7-diphenyl-1,10-phenanthroline), LiF, MgF$_2$, phenanthroline-based compounds, e.g., BCP manufactured by UDC Co., Ltd., imidazoles, triazoles, oxadiazoles, e.g., PBD, aluminum complexes manufactured by UDC Co., Ltd., BAlq (Aluminum(III) bis (2-methyl-8-quinolinato) 4-phenylpheolate), as represented by the following formula:

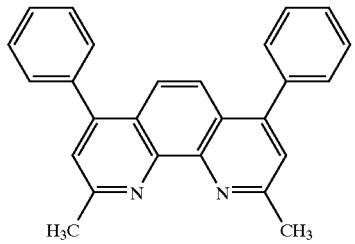

Phenanthroline-containing organic compound

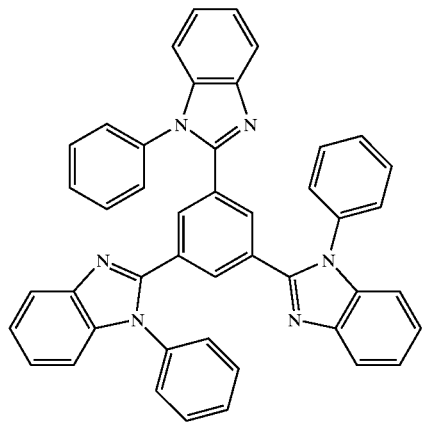

Imidazole-containing organic compound

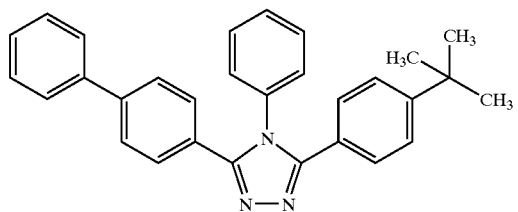

Triazole-containing organic compound

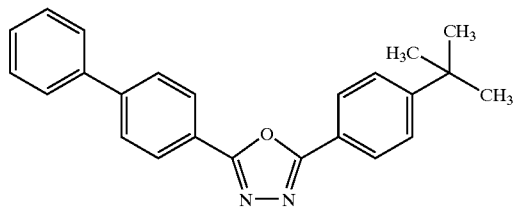

Oxidiazole-containing organic compound

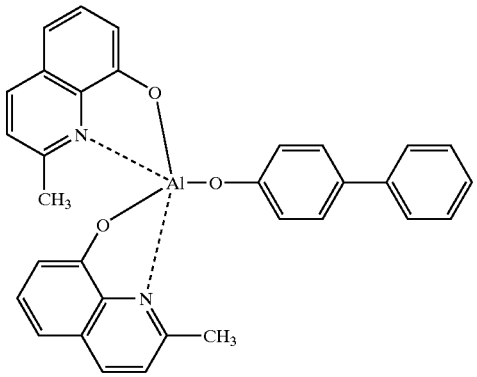

Examples of materials suitable for forming the electron transport layer 15 include oxazoles, isooxazoles, triazoles, isothiazoles, oxadiazoles, thiadiazoles, perylenes, aluminum complexes, e.g., Alq3 (tris(8-quinolinolato)-aluminium), BAlq, SAlq, or Almq3, and gallium complexes, e.g., Gaq'2OPiv, Gaq'2OAc or 2(Gaq'2), as represented by the following formula.

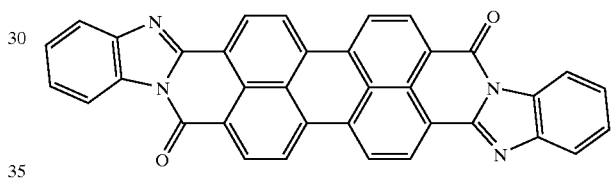

Perylene compound

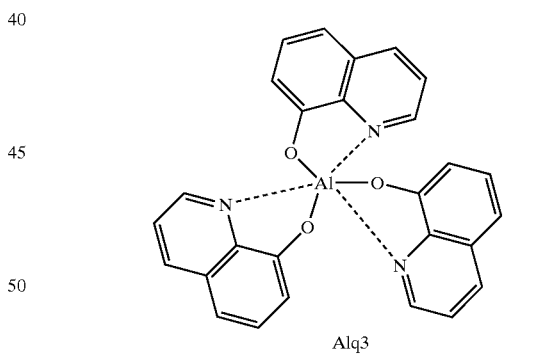

Alq3

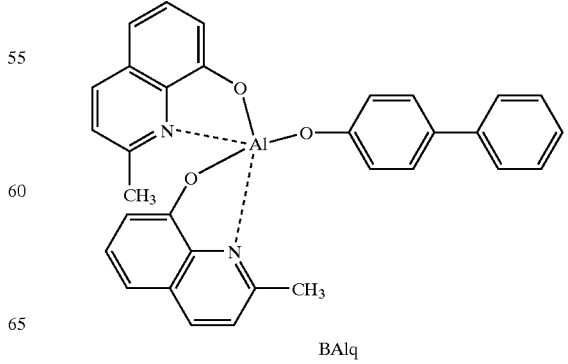

BAlq

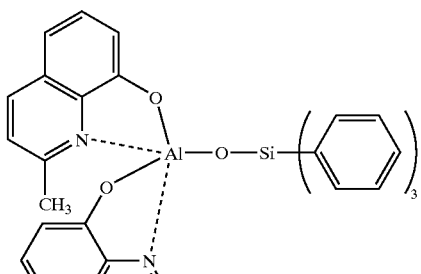

SAlq

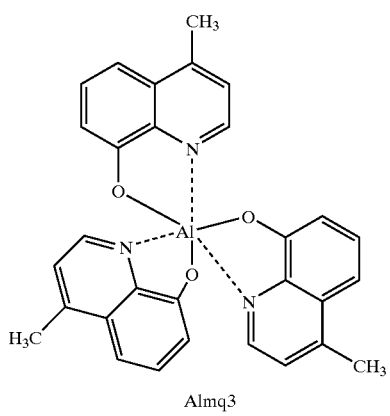

Almq3

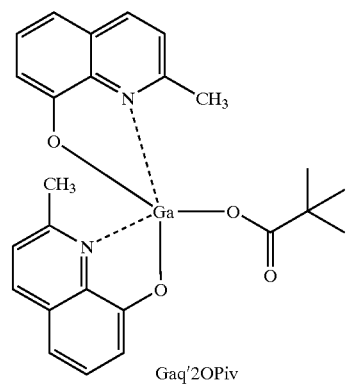

Gaq'2OPiv

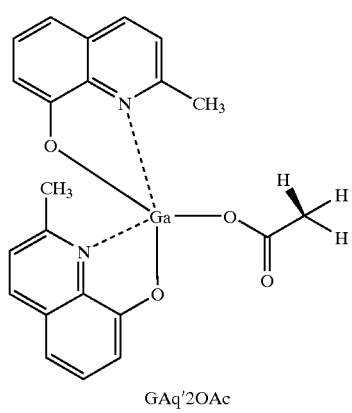

GAq'2OAc

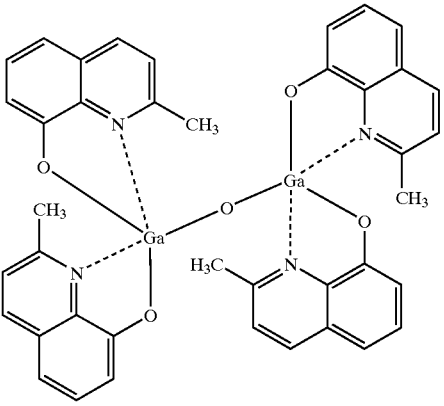

2(Gaq'2)

The thickness of the hole blocking layer 13 preferably is within the range of from about 100 to about 1000 Å, and the thickness of the electron transport layer 15 is preferably within the range of from about 100 to about 1000 Å. If the thicknesses of the hole blocking layer 13 and the electron transport layer 15 are not in the ranges specified above, hole blocking capability and electron transport capability may be undesirably poor.

A second electrode 14 then preferably is formed on the resultant product, followed by encapsulating, thereby completing an organic EL device. Materials suitable for forming the second electrode 14 are not particularly limited, and include metals having a low work function, for example, Li, Ca, Ca/Al, LiF/Ca, LiF/Al, Al, Mg, Mg alloy, which can be used for deposition. The thickness of the second electrode 14 preferably is within the range of from about 50 to about 3000 Å.

The diphenyl anthracene derivative represented by formula 1 according to the present invention can be used not only as the material for forming an emissive layer in manufacturing the organic EL device, but also as the material for forming the hole injection layer or the hole transport layer.

The present invention will be described in greater detail with reference to the following examples. The following examples are for illustrative purposes and are not intended to limit the scope of the invention.

FIG. 1A schematically shows a method of preparing a compound represented by formula 1a, which now will be described in more detail.

PREPARATION EXAMPLE 1

Compound Represented by Formula 1a
(R is n-octyl)

1. Preparation of Compound (1)

$K_2CO_3$ (48.4 g (350 mmol)) was added to a solution of 50 g (290 mmol) of 4-bromophenol dissolved in 500 mL of acetone, and 73.3 g (380 mmol) of 1-bromooctane was added to the mixture and refluxed for 24 hours. After the reaction was completed, the reaction mixture was extracted using a 2:1 mixture of water and chloroform ($CHCl_3$) by volume to remove $K_2CO_3$. The organic layers were dried using $MgSO_4$, concentrated, and subjected to silica gel column chromatography using n-hexane as an eluent. A resulting eluate was distilled under reduced pressure to remove unreacted 1-bromooctane and to produce 80 g of Compound (1) with a yield of 96%. The structure of Compound (1) was identified through $^1$H-NMR.

2. Preparation of Compound (2)

Compound (1) (38 g (130 mmol)) was dissolved in 150 mL of anhydrous THF. The mixture was cooled to approximately −75° C., and 100 mL (1.2 eq) of n-butyl lithium was added thereto slowly and stirred for 1 hour. 2-isopropoxy-4,4,5,5-tetramethyl-1,3,2-dioxaborolane (32.9 g (1.3 eq)) then was added to the reaction mixture and reacted for 1 hour.

After the reaction was completed, the reaction mixture was extracted three times using a 2:1 mixture of water and ethyl acetate by volume. The filtered organic layers were dried using $MgSO_4$, concentrated, and distilled under reduced pressure to remove unreacted 2-isopropoxy-4,4,5,5-tetramethyl-1,3,2-dioxaborolane to produce Compound (2). The structure of Compound (2) was identified through $^1$H-NMR.

3. Preparation of Compound (3)

To a 500 mL round-bottomed flask were added 33 g (2.3 eq) of Compound (2), 17 g (0.05 mol) of 9,10-dibromoanthracene), 0.87 g (1.5 mol % of 9,10-dibromoanthracene of tetrakis(triphenylphosphine) palladium ($Pd(PPh_3)_4$) and 150 mL of a 2M $Na_2CO_3$ aqueous solution, and 100 mL of anhydrous toluene was added thereto for dissolution of solid matter, followed by reacting at 100° C. for 36 hours.

After the reaction was completed, the reaction mixture was extracted with a 2:1 mixture of water and ethyl acetate by volume. The organic layers were dried using $MgSO_4$. Activated carbon was added to the dried organic layers, stirred for 2 hours to remove colors, filtered and concentrated. The concentrated solution was recrystallized in a 1:1 mixed solvent of acetone and methanol by volume to provide 24 g of Compound (3) with a yield of 84%. The structure of Compound (3) was identified through $^1$H-NMR.

4. Preparation of Compound (4)

Compound (3) (5 g (8.5 mmol)) was added to 100 mL of chloroform in a 250 mL round-bottomed flask, and stirred while slowly adding 2.8 g (2.1 eq) of bromine at 0° C. When the complete consumption of Compound (3) was confirmed through TLC, addition of bromine was stopped, and the reaction mixture was stirred for 30 min. A small amount of acetone then was added to the reaction mixture to quench bromination.

After the reaction, the mixture was washed using water, dried using $MgSO_4$, concentrated, and re-precipitated in methanol to provide 4.8 g of Compound (4) with a yield of 75%. The structure of Compound (4) was identified through $^1$H-NMR. $^1$H-NMR(CDCl$_3$, δ) 0.63–1.44(m, 30H, 2-(CH$_2$)$_6$CH$_3$), 3.81(t, 4H, 2-OCH$_2$—), 6.96–7.75(m, 14H, Aromatic Protons).

5. Preparation of Compound Represented by Formula 1a

Compound (4) (4 g (5.37 mmol)), 1.98 g (11.82 mmol) of 9-H-Carbazole, 0.197 g (2.15×10$^{-4}$ mol) of Pd$_2$(dba)$_3$, 1.6 g (1.61×10$^{-2}$ mol) of NaOtBu, and 0.0663 mL (2.69×10$^{-4}$ mol) of (t-Bu)$_3$P were added to a 250 mL round-bottom flask under nitrogen atmosphere, and 100 mL of anhydrous toluene was added thereto. The temperature of the reaction mixture was elevated to approximately 110° using an oil bath, and stirred for approximately 48 hours.

Figure 3:
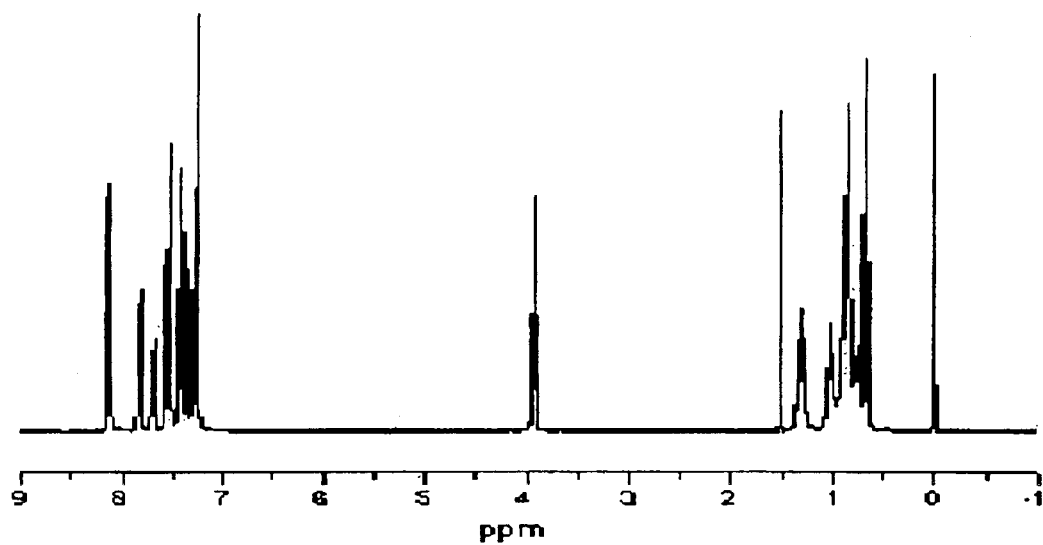
FIG. 3 is a $^1$H-NMR spectrum of the compound represented by formula 1a according to Synthesis Example 1 herein.

After the reaction was completed, the reaction product was worked up using water and chloroform and organic layers were washed using 500 mL of a 1N HCl aqueous solution. The resultant product was distilled under reduced pressure to remove any organic solvent, providing a solid. The obtained solid was dissolved again in toluene, primarily refined using silica gel column chromatography, recrystallized using n-hexane and methylene chloride, thus producing 3.94 g of Compound represented by formula 1a with a yield of 80%. The $^1$H-NMR structure of Compound represented by formula 1a is shown in FIG. 3. $^1$H-NMR(CDCl$_3$, δ) 0.56–1.44(m, 30H, 2-(CH$_2$)$_6$CH$_3$), 3.91(t, 4H, 2-OCH$_2$—), 7.14–8.24(m, 30H, Aromatic Protons).

Figure 1B:
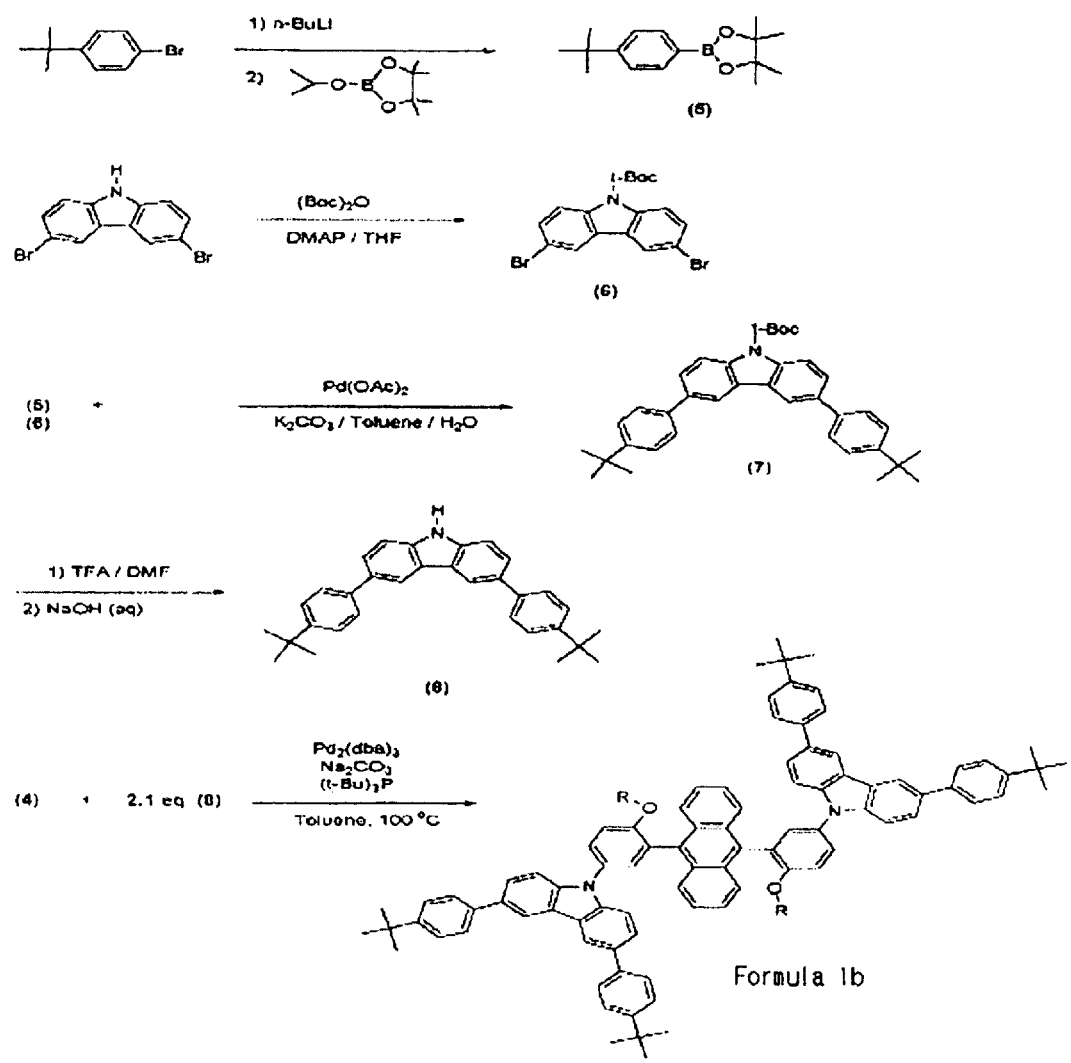
FIG. 1B is a reaction scheme illustrating the synthesis of a compound represented by formula 1b according to Synthesis Example 2 herein.

FIG. 1B schematically shows a preparation process of a compound represented by formula 1b, which will now be described in more detail.

PREPARATION EXAMPLE 2

Compound Represented by Formula 1b
(R is n-octyl)

1. Preparation of Compound (5)

1-bromo-4-t-butylbenzene (47.5 g (0.223 mol)) was dissolved in 500 mL of anhydrous THF and the reaction product was cooled to approximately −70° C. 2.5M n-butyl lithium (127.4 mL (0.3185 mol)) then was slowly added to the reaction mixture, stirred for approximately 30 minutes, and 50 mL (0.245 mol) of 2-isoproxy-4,4,5,5-tetramethyl-1,3,2-dioxaborolan was added and stirred for approximately 1 hour.

After the reaction was completed, 500 mL of distilled water was added to the reaction mixture to precipitate a while compound. The white solid was filtered, washed with 200 mL of distilled water and dried under reduced pressure, yielding 43 g of Compound (5). The structure of Compound (1) was identified through $^1$H-NMR.

2. Preparation of Compound (6)

9-H-3,3-dibromocarbazol (70 g (0.22 mol)) was dissolved in a 1 L flask containing 1 L of THF, 56.7 g (0.26 mol) of (Boc)$_2$O and 3.2 g (0.026 mol) of DMAP(4-dimethylaminopyridine) was added and stirred for approximately 12 hours.

After the reaction was completed, 1 L of ethyl acetate and 1 L of water were added to the obtained precipitate to filter the organic layers. The obtained organic layers were washed with 1 L of 1N HCl aqueous solution, 1 L of water, and 1 L of NaHCO$_3$ aqueous solution and dried under reduced pressure to yield 75 g of white solid, which was Compound (6). The structure of Compound (6) was identified through $^1$H-NMR.

3. Preparation of Compound (7)

Compound (5)(49 g (0.188 mol)) and 24 g (0.055 mol) of Compound (6) were added to 300 mL of toluene, and then 200 mL of distilled water, 1.2 g (5.5 mol) of Pd(OAc)$_2$ and 53 g of K$_2$CO$_3$ 53 g were added thereto, followed by stirring at 70° C. for 16 hours.

After the reaction was completed, the reaction mixture was extracted using 400 mL of ethyl acetate and concentrated under reduced pressure. The obtained precipitate was used for the immediately next reaction. The structure of Compound (7) was identified through $^1$H-NMR.

4. Preparation of Compound (8)

TFA (Trifluoroacetic acid −30 mL) and 100 mL of DMF were added to the remainder and stirred at 100° C. for approximately 48 hours. After the reaction was completed, the reaction mixture was concentrated under reduced pressure to remove TFA.

A 2N aqueous solution of NaOH (100 mL) and 100 mL of water were added to the reaction mixture to produce a white solid compound. The obtained compound was filtered and washed with 100 mL of ethyl acetate to yield 20 of Compound (8). The structure of Compound (8) was identified through $^1$H-NMR. $^1$H-NMR(DMSO-d$_6$, δ) 1.33(m, 18H, 2-C(CH$_3$)$_3$), 3.91(t, 4H, 2-OCH$_2$—), 7.20–8.75(m, 14H, Aromatic Protons), 11.3(s, 1H, —N—H of carbazole).

5. Preparation of Compound Represented by Formula 1b

Compound (4) (1.2 g (1.6 mmol)), 1.426 g (3.3 mmol) of Compound (8), 0.059 g (0.64×10$^{-4}$ mol) of Pd$_2$(dba)$_3$, 0.465 g (4.835×10$^{-3}$ mol) of NaOtBu, 0.016 mL (0.81×10$^{-4}$ mol) of (t-Bu)$_3$P and 40 mL of anhydrous toluene were added to a 100 mL round-bottom flask under nitrogen atmosphere. The temperature of the reaction mixture was elevated to approximately 110° C. using an oil bath, and stirred for approximately 48 hours.

Figure 4:
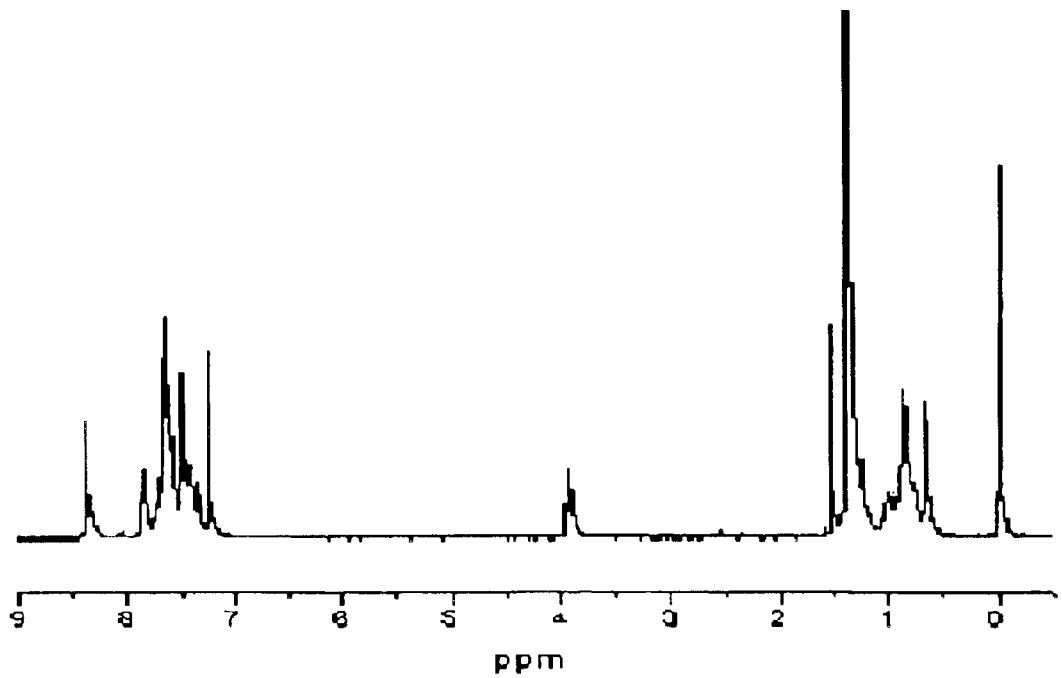
FIG. 4 is a $^1$H-NMR spectrum of the compound represented by formula 1b according to Synthesis Example 2 herein.

After the reaction was completed, the reaction product was worked up using water and chloroform and washed using 500 mL of a 1N aqueous solution of hydrochloric acid. Organic layers were removed under reduced pressure, thereby providing a solid. The obtained solid was re-crystallized using a 3:1 mixture of n-hexane and toluene by volume, thus producing 1.86 g of a compound represented by formula 1b with a yield of 80%. The $^1$H-NMR structure of the compound represented by formula 1b is shown in FIG. 4. $^1$H-NMR(CDCl$_3$, δ) 0.52–1.45[m, 48H, 2-(CH$_2$)$_6$CH$_3$] & 2-C(CH$_3$)$_3$], 3.93(t, 4H, 2-OCH$_2$—), 7.10–8.44(m, 42H, Aromatic Protons).

PREPARATION EXAMPLE 3

Compound Represented by Formula 1c

Compound (4) (4 g (5.37 mmol)), 2.00 g (11.82 mmol) of N,N-dipyhenylamine, 0.197 g (2.15×10$^{-4}$ mol) of Pd$_2$(dba)$_3$, 1.6 g (1.61×10$^{-2}$ mol) of NaOtBu and 0.0663 mL (2.69×10$^{-4}$ mol) of (t-Bu)$_3$P were added to a 250 mL round-bottom flask under nitrogen atmosphere and 100 mL of anhydrous toluene was added thereto. The temperature of the reaction mixture was elevated to approximately 110° C. using an oil bath, and stirred for approximately 48 hours.

After the reaction was completed, the reaction product was worked up using water and chloroform and organic layers were washed using 500 mL of a 1N solution of hydrochloric acid. The resultant product was distilled under reduced pressure to remove an organic solvent, thereby providing a solid. The obtained solid was dissolved again in toluene, primarily refined using silica gel column chromatography, re-crystallized using n-hexane and methylene chloride, thereby producing 3.95 g of a compound represented by formula 1c, that is, 9,10-bis(2-n-octyloxy-5-diphenylaminophenyl) anthracene, with a yield of 80%. $^1$H-NMR(CDCl$_3$, δ) 0.55–1.43(m, 30H, 2-(CH$_2$)$_6$CH$_3$), 4.01 (t, 4H, 2-OCH$_2$—), 7.05–7.82(m, 34H, Aromatic Protons).

The compound represented by formula 1b (R: n-octyl) prepared in Preparation Example 2 was dissolved in chlorobenzene, and the resultant solution was spin-coated on a quartz substrate and dried to form a thin film. UV-VIS spectrum and PL (photoluminescence) spectrum of the obtained film were measured and the results are shown in FIG. 5.

Figure 5:
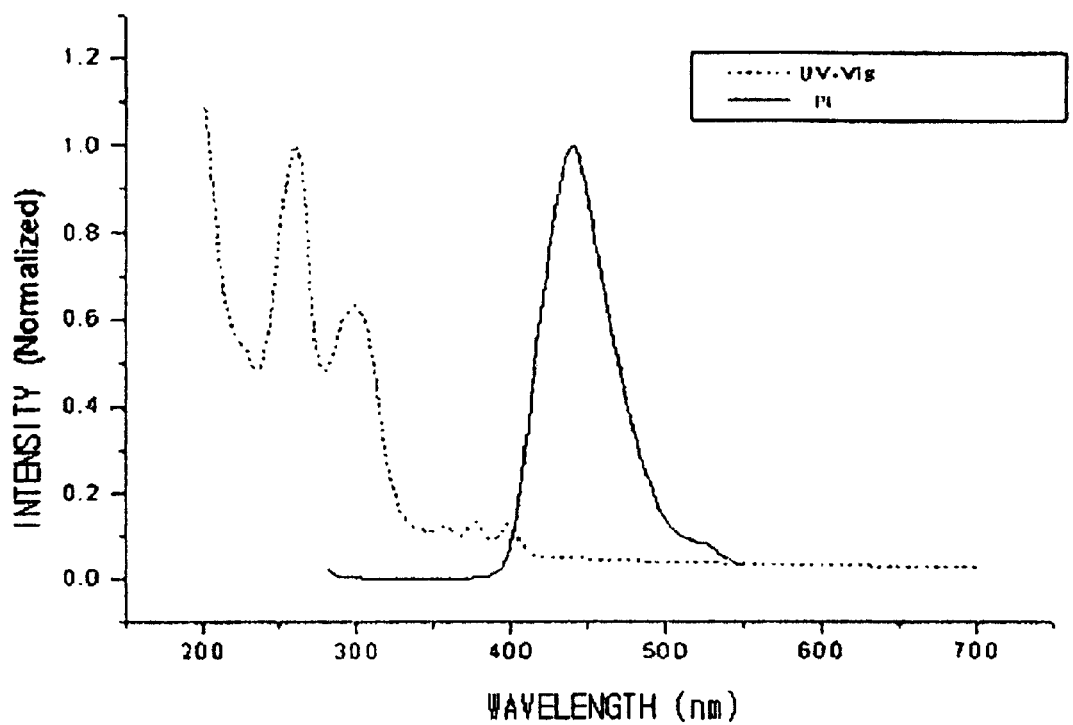
FIG. 5 is UV-Vis and PL (photoluminescent) spectra of the compound represented by formula 1b according to Synthesis Example 2 herein.

Referring to FIG. 5, the UV-VIS absorption spectrum showed that the compound represented by formula 1b (R: n-octyl) exhibited three characteristic peaks of substantially the same size, that is, 357 nm, 377 nm and 398 nm. The maximum PL peak measured using the maximum absorption wavelength as the excitation wavelength was approximately 442 nm.

Figure 8:
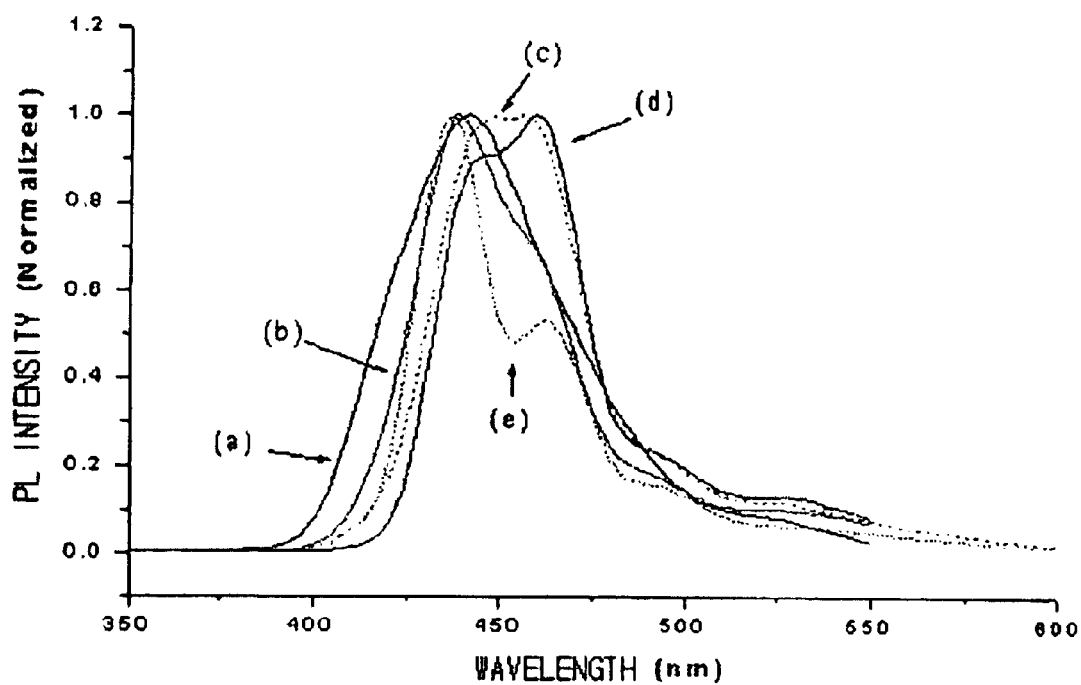
FIG. 8 is a PL spectra of blends of the compound represented by formula 1b according to Synthesis Example 2 herein and poly(9,9-dioctylfluorene) (PC8F): (a) 100%, (b) 70%, (c) 30%, (d) 10% of the compound represented by formula 1b and (e) PC8F.

The photoluminescent (PL) spectrum depending on the blend ratio of the compound represented by formula 1b (R: n-octyl) and PC8F [poly(9,9-dioctylfluorene)] by weight was examined and the results thereof are shown in FIG. 8. FIG. 8(a) shows the PL spectrum of pure compound represented by formula 1b (R: n-octyl), FIG. 8(b) shows the emission spectrum of a 30:70 blend of the compound represented by formula 1b (R: n-octyl) and PC8F by weight, FIG. 8(c) shows the emission spectrum of a 20:80 blend of the compound represented by formula 1b (R: n-octyl) and PC8F by weight, FIG. 8(d) shows the emission spectrum of a 10:90 blend of the compound represented by formula 1b (R: n-octyl) and PC8F by weight, and FIG. 8(e) shows the emission spectrum of pure PC8F film (spin-coated on quartz substrate).

The thermal properties of the Compound represented by formula 1b (R: n-octyl) prepared in Preparation Example 2 were examined by TGA (Thermogravimetric analysis) and DSC (Differential Scanning Calorimetry). The thermal properties were measured under nitrogen atmosphere at a speed of 10° C./min.

Figure 6:
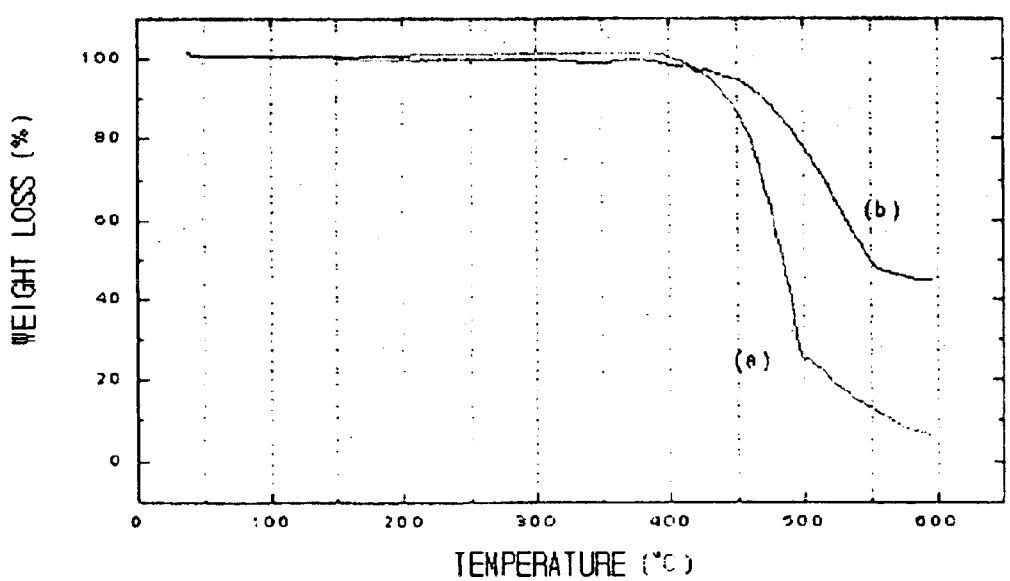
FIG. 6 is a thermogravimetric analysis (TGA) graph of α-NPB (a) and the compound represented by formula 1b according to Synthesis Example 2 herein.

The results of TGA and DSC are shown in FIGS. 6 and 7. FIG. 6(a) shows thermal properties of α-NPB[N,N'-bis (naphthalene-1-yl)-N,N'-diphenylbenzidine], which generally is used as a hole transport material, and FIG. 6(b) shows thermal properties of Compound represented by formula 1b. Referring to FIGS. 6(a) and 6(b), α-NPB experienced a loss in weight of 5% at approximately 432° C. and approximately 50% by weight of the compound remained at approximately 484° C.

On the other hand, the compound represented by formula 1b experienced a loss in weight of 5% at approximately 453° C. and approximately 50% by weight of the compound remained at approximately 550° C., that is, relatively high thermal stability was exhibited.

Figure 7A:
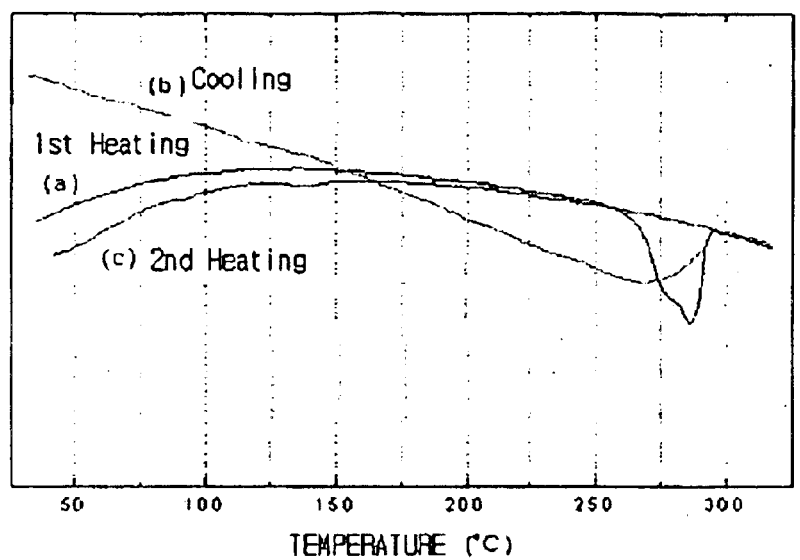
FIG. 7A is a differential scanning calorimeter (DSC) graph of the compound represented by formula 1b according to Synthesis Example 2 herein.
Figure 7B:
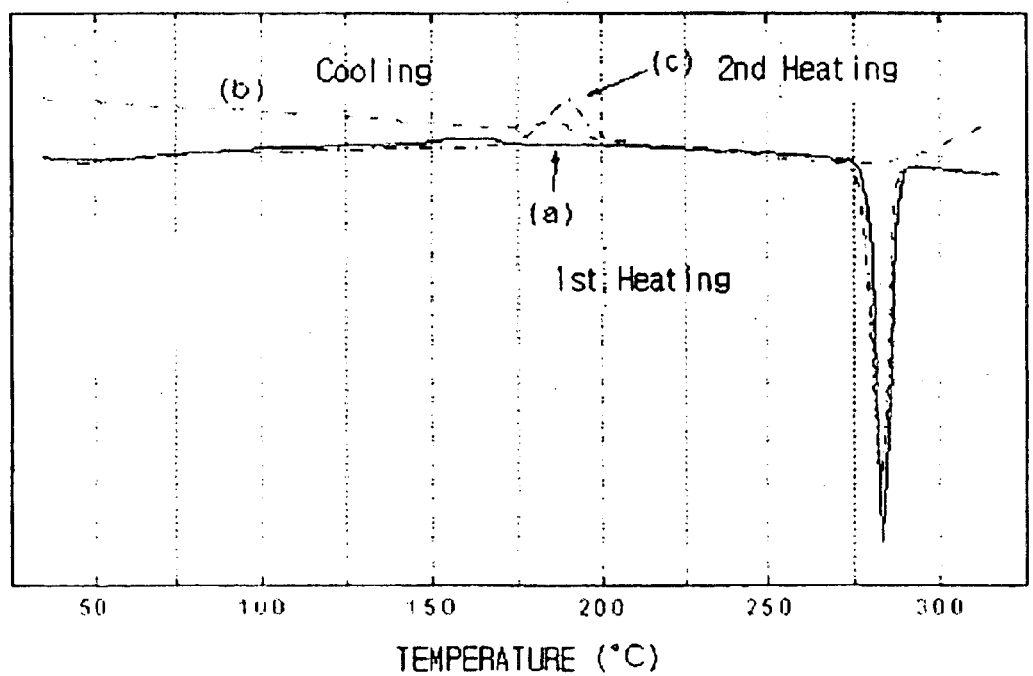
FIG. 7B is a DSC graph of α-NPB.

Referring to FIG. 7A, while most low-molecular weight EL materials have distinct melting points (even after melting followed by rapid re-crystallization: eg. FIG. 7B for α-NPB), the compound represented by formula 1b was neither re-crystallized nor melted in the course of recooling and reheating once melted at approximately 287° C., thereby suggesting that the compound represented by formula 1b became completely noncrystalline once melted. A thin film was manufactured by spin coating and no crystallized area was observed from the surface of the thin film through a polarization microscope.

EXAMPLE 1

Manufacture of Organic EL Device

A transparent electrode layer coated with indium-tin oxide (ITO) was cleaned. The ITO layer was patterned into a desired shape using a photoresist resin and etchant to form an ITO electrode pattern, and washed. Poly(styrene sulfonate)-doped poly(3,4-ethylenedioxy thiophene (PEDOT) (available from Bayer Co. in the trade name of BATRON® P 4083) was coated on the patterned ITO layer to a thickness of 500 Å and baked at 180° C. for about 1 hour to form a hole injection layer.

A 10:90 mixture of 0.01 g of the compound represented by formula 1b prepared in Preparation Example 2, and 0.09 g of PC8F, by weight, was dissolved in 4.90 g of chlorobenzene to obtain an EL layer composition. The EL layer composition was spin coated on the hole injection layer, baked at 90° C. for 2 hours, and placed in a vacuum oven to fully remove the solvent, forming an emissive layer to a thickness of approximately 800 Å.

Figure 9:
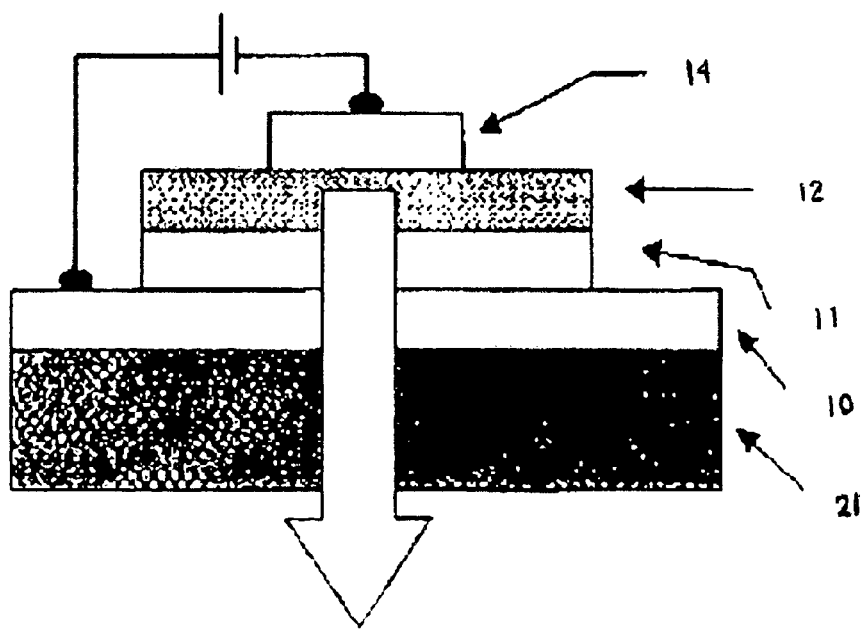
FIG. 9 is a schematic view illustrating the structure of an organic EL device manufactured in example 1 herein.

Then, calcium and aluminum were sequentially deposited on the emissive layer in a vacuum deposition chamber at a vacuum of $4 \times 10^{-6}$ torr to form a cathode having a thickness of from about 2500 to about 3000 Å, followed by encapsulating, thereby manufacturing an organic EL device. The thickness and growth rate of layers during the deposition were controlled using a crystal sensor. The resulting EL device had a single stack structure, as illustrated in FIG. 9, where the numerals in FIG. 9 refer to like embodiments as discussed with reference to FIG. 2 above. The emissive area was 6 mm$^2$.

EXAMPLE 2

Manufacture of Organic EL

An organic EL device was manufactured in the same manner as in Example 1, except that a 20:80 blend of 0.02 g of the compound represented by formula 1b prepared in Preparation Example 2 and 0.08 g of PC8F, by weight, was used instead of a 10:90 blend, to prepare an emissive layer.

EXAMPLE 3

Manufacture of Organic EL

An organic EL device was manufactured in the same manner as in Example 1, except that a 30:70 blend of 0.03 g of the compound represented by formula 1b prepared in Preparation Example 2 and 0.07 g of PC8F, by weight, was used instead of a 10:90 blend, to prepare an emissive layer.

EXAMPLE 4

Manufacture of Organic EL

An organic EL device was manufactured in the same manner as in Example 1, except that only 0.1 g of the compound represented by formula 1b prepared in Preparation Example 2 was used instead of a 10:90 blend of the compound represented by formula 1b prepared in Preparation Example 2 and PC8F, by weight, to prepare an emissive layer.

COMPARATIVE EXAMPLE 1

Manufacture of an Organic EL Device

An EL device was manufactured in the same manner as in Example 1, except that only 0.1 g of PC8F was used instead of a 10:90 blend of the compound represented by formula 1b prepared in Preparation Example 2 and PC8F, by weight, to prepare an emissive layer.

Figure 10:
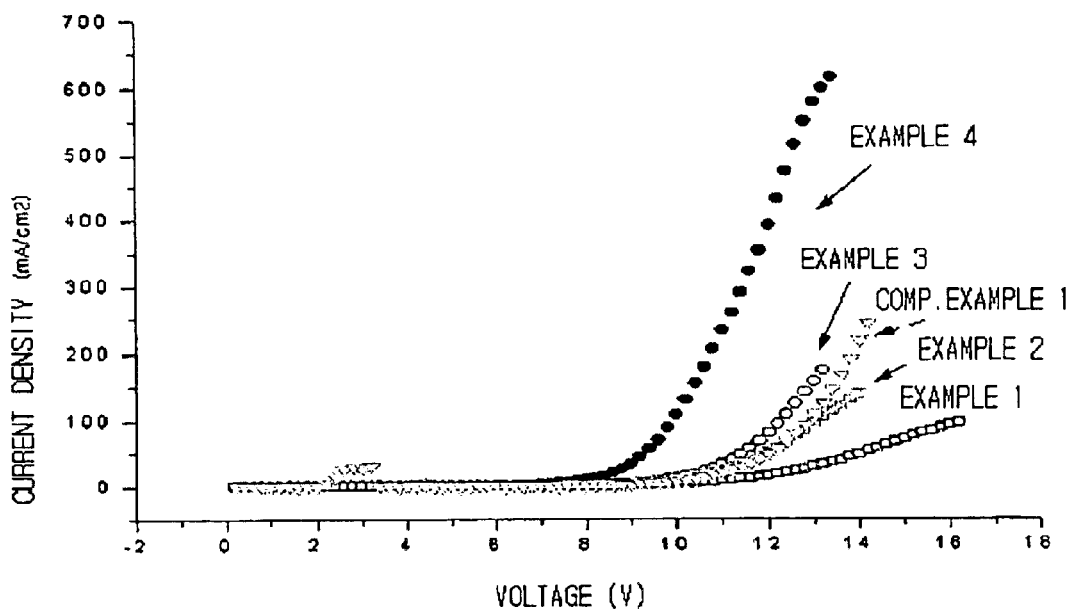
FIG. 10 is a graph of current density versus applied voltage for EL devices manufactured in examples 1–4 herein and Comparative Example 1.
Figure 11:
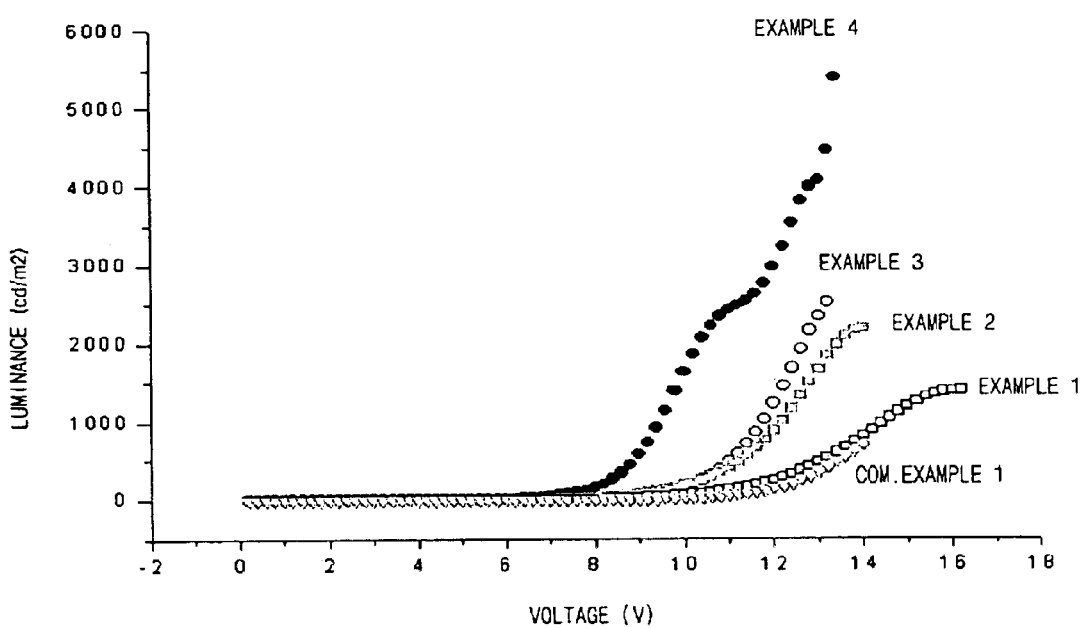
FIG. 11 is a graph of luminance versus applied voltage for EL devices manufactured in examples 1–4 herein and Comparative Example 1.
Figure 12:
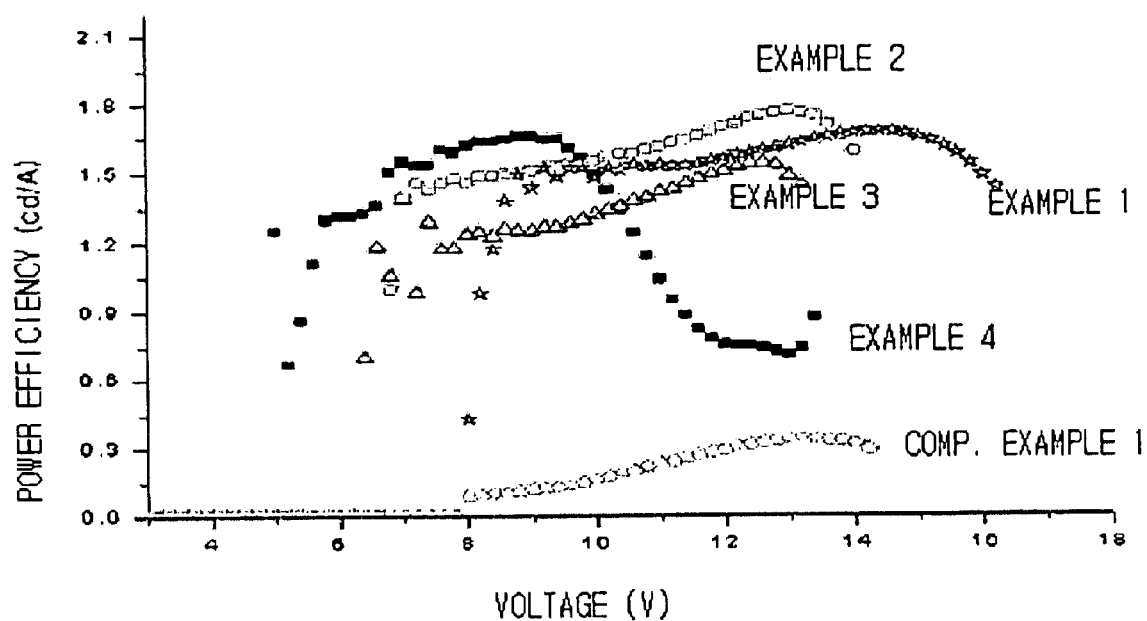
FIG. 12 is a graph of EL efficiency versus applied voltage for EL devices manufactured in examples 1–4 invention and Comparative Example 1.

The color coordinate properties and EL properties of the organic EL devices of Examples 1–4 and Comparative Example 1 were measured, and the results are shown in FIGS. 10–12. For measurement of EL properties, a forward bias voltage was applied as a direct current (DC) driving voltage.

The organic EL devices of Examples 1–4 and Comparative Example 1 exhibited typical rectifying diode characteristics. In the respective devices, driving voltages ranged 5.5~7.5 V, the maximum luminance ranged 713~5392 cd/m$^2$, and the maximum quantum efficiency ranged from about 0.34 to about 1.66 cd/A. Also, the organic EL devices exhibited stability even after repeated driving cycles, that is, voltage-current density characteristics were maintained at initial levels.

The EL properties of the organic EL devices of Examples 1–4 and Comparative Example 1 are summarized in Table 1.

TABLE 1

|  | Amount of PC8F (wt %) 100 | Amount of Compound represented by formula 1b (wt %) | | | |
| --- | --- | --- | --- | --- | --- |
|  | (Comparative Example 1) | 10 (Example 1) | 20 (Example 2) | 30 (Example 3) | 100 (Example 4) |
| Maximum efficiency (cd/A) | 0.34 | 1.68 | 1.77 | 1.54 | 1.66 |
| Maximum luminance (cd/m$^2$) | 713 | 1382 | 2170 | 2508 | 5392 |
| Relative efficiency (Cd/A) @100 cd/m$^2$ | 0.28 | 1.53 | 1.53 | 1.28 | 1.6 |

As shown in Table 1, when the compound represented by formula 1b was used alone as an emissive layer, the efficiency and luminance characteristics were the highest. Compared when PC8F was used alone, when 10% by weight of the compound represented by formula 1b was mixed with PC8F to prepare an emissive layer, the maximum efficiency and the relative efficiency at 100 nit were improved approximately 5 times and 6 times, respectively.

As described above, a diphenyl anthracene derivative according to the present invention is useful as a blue emissive compound. More specifically, such a compound comprising a 9,10-diphenyl anthracene unit in its backbone and having alkoxy groups and substituted or unsubstituted amino groups introduced to 2 and 5 positions of phenyl in the diphenyl anthracene unit, exhibits thermal stability and crystalline stability. Also, the diphenyl anthracene derivative is easily purified to a high degree, and a thin film can be easily obtained therefrom using a soluble solvent. In addition, when the blue EL polymer according to the present invention is used for organic layers, an organic EL device with improved luminance, driving voltage and efficiency can be manufactured.

The present invention has been described with reference to particularly preferred embodiments and examples. Those skilled in the art will appreciate that various modifications may be made to the invention without departing from the spirit and scope thereof.

What is claimed is:

1. A diphenyl anthracene derivative represented by formula 1:

<Formula 1>

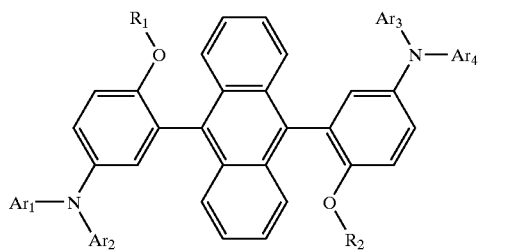

wherein $R_1$ and $R_2$ are independently a hydrogen atom; a $C_{1-20}$ linear or branched alkyl group; a $C_{5-20}$ cycloalkyl group; a $C_{6-20}$ aryl group; a $C_{4-20}$ heteroaryl group; or a $C_{6-20}$ aryl group having at least one substituent selected from the group consisting of a halogen atom, a $C_{1-10}$ halogenated alkyl group, —Si(R)(R')(R"), a $C_{1-10}$ alkyl group, a $C_{1-10}$ alkoxy group, a $C_{6-10}$ aryl group, a $C_{4-10}$ heteroaryl group and —N(R)(R'), $Ar_1$, $Ar_2$, $Ar_3$ and $Ar_4$ are independently a hydrogen atom; a $C_{1-20}$ linear or branched alkyl group; a $C_{5-20}$ cycloalkyl group; a $C_{6-20}$ aryl group; a $C_{4-20}$ heteroaryl group; or a $C_{6-20}$ aryl group having at least one substituent group selected from the group consisting of a halogen atom, a $C_{1-10}$ halogenated alkyl group, —Si(R)(R')(R"), a $C_{1-10}$ alkyl group, a $C_{1-10}$ alkoxy group, a $C_{6-10}$ aryl group, a $C_{4-10}$ heteroaryl group and —N(R)(R'), where at least one selected from the group consisting of $Ar_1$ and $Ar_2$, and $Ar_3$ and $Ar_4$ can be interconnected, respectively, and R, R' and R" are independently selected from the group consisting of a hydrogen atom, a $C_{1-10}$ alkyl group, a $C_{1-10}$ alkoxy group, a $C_{6-10}$ aryl group and a $C_{4-10}$ heteroaryl group.

2. The diphenyl anthracene derivative as claimed in claim 1, wherein in formula 1, —N($Ar_1$)($Ar_2$) and —N($Ar_3$)($Ar_4$) are independently a group represented by formula 2:

<Formula 2>

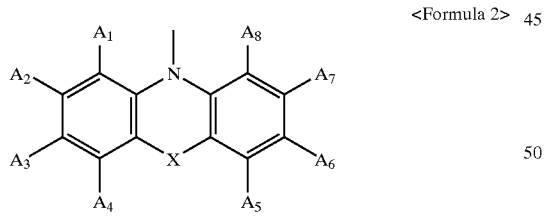

wherein X is —(CH$_2$)$_n$—, where n is an integer of 0~2, —C($R_3$)($R_4$)—, —CH=CH—, —S—, —O— or —Si($R_3$)($R_4$)—, $A_1$, $A_2$, $A_3$, $A_4$, $A_5$, $A_6$, $A_7$, $A_8$, $R_3$, and $R_4$ are independently a hydrogen atom; a $C_{1-20}$ linear or branched alkyl group; a $C_{5-20}$ cycloalkyl group; a $C_{6-20}$ aryl group; a $C_{4-20}$ heteroaryl group; or a $C_{6-20}$ aryl group having at least one substituent selected from the group consisting of a halogen atom, a $C_{1-10}$ halogenated alkyl group, —Si(R)(R')(R"), a $C_{1-10}$ alkyl group, a $C_{1-10}$ alkoxy group, a $C_{6-10}$ aryl group, a $C_{4-10}$ heteroaryl group and —N(R)(R'), at least one selected from the group consisting of $A_1$ and $A_2$, $A_2$ and $A_3$, $A_3$ and $A_4$, $A_5$ and $A_6$, $A_6$ and $A_7$, and $A_7$ and $A_8$ can be interconnected, respectively, and R, R' and R" are independently selected from the group consisting of a hydrogen atom, a $C_{1-10}$ alkyl group, a $C_{1-10}$ alkoxy group, a $C_{6-10}$ aryl group and a $C_{4-10}$ heteroaryl group.

3. The diphenyl anthracene derivative as claimed in claim 2, wherein the group represented by formula 2 is at least one selected from the group consisting of groups (2a)–(2h):

(2a)
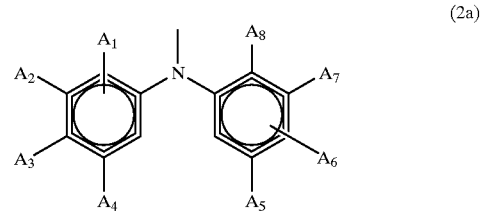

(2b)
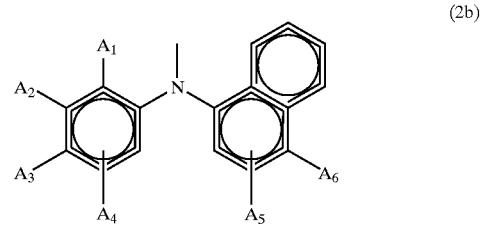

(2c)
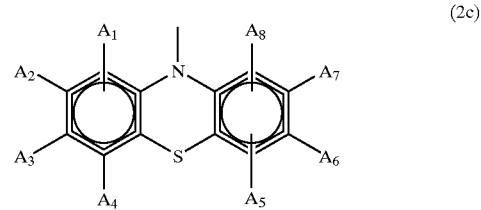

(2d)
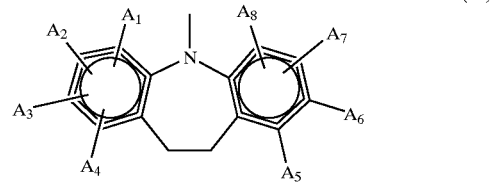

(2e)
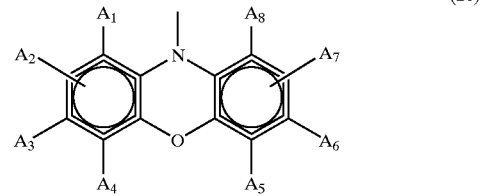

(2f)
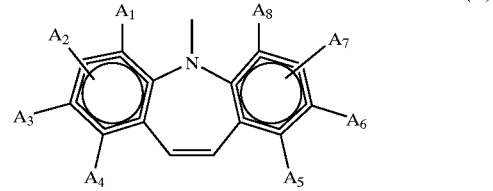

-continued (2g)
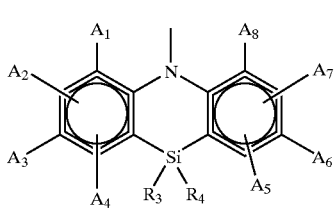

(2h)
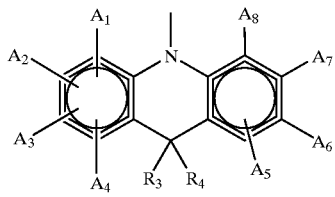

wherein $A_1$, $A_2$, $A_3$, $A_4$, $A_5$, $A_6$, $A_7$, $A_8$, $R_3$ and $R_4$ are independently a hydrogen atom; a $C_{1-20}$ linear or branched alkyl group; a $C_{5-20}$ cycloalkyl group; a $C_{6-20}$ aryl group; a $C_{4-20}$ heteroaryl group; or a $C_{6-20}$ aryl group having at least one substituent selected from the group consisting of a halogen atom, a $C_{1-10}$ halogenated alkyl group, —Si(R)(R')(R"), a $C_{1-10}$ alkyl group, a $C_{1-10}$ alkoxy group, a $C_{6-10}$ aryl group, a $C_{4-10}$ heteroaryl group and —N(R)(R'), at least one selected from the group consisting of $A_1$ $A_1$ and $A_2$, $A_2$ and $A_3$, $A_3$ and $A_4$, $A_5$ and $A_6$, $A_6$ and $A_7$, and $A_7$ and $A_8$ can be interconnected, respectively, and R, R' and R" are independently selected from the group consisting of a hydrogen atom, a $C_{1-10}$ alkyl group, a $C_{1-10}$ alkoxy group, a $C_{6-10}$ aryl group and a $C_{4-10}$ heteroaryl group.

4. The diphenyl anthracene derivative as claimed in claim 1, wherein in formula 1, —N(Ar$_1$)(Ar$_2$) and —N(Ar$_3$)(Ar$_4$) are independently a group represented by formula 3:

<Formula 3>
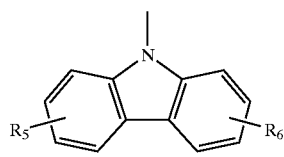

wherein $R_5$ and $R_6$ are independently a hydrogen atom; a $C_{1-20}$ linear or branched alkyl group; a $C_{5-20}$ cycloalkyl group; a $C_{6-20}$ aryl group; a $C_{4-20}$ heteroaryl group; or a $C_{6-20}$ aryl group having at least one substituent group selected from the group consisting of a halogen atom, a $C_{1-10}$ halogenated alkyl group, —Si(R)(R')(R"), a $C_{1-10}$ alkyl group, a $C_{1-10}$ alkoxy group, a $C_{6-10}$ aryl group, a $C_{4-10}$ heteroaryl group and —N(R)(R'), and R, R' and R" are independently selected from the group consisting of a hydrogen atom, a $C_{1-10}$ alkyl group, a $C_{1-10}$ alkoxy group, a $C_{6-10}$ aryl group and a $C_{4-10}$ heteroaryl group.

5. The diphenyl anthracene derivative as claimed in claim 4, wherein in formula 3, $R_5$ and $R_6$ are represented by formula 4:

<Formula 4>
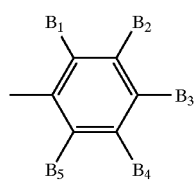

wherein $B_1$, $B_2$, $B_3$, $B_4$ and $B_5$ are independently a hydrogen atom; a $C_{1-20}$ linear or branched alkyl group; a $C_{5-20}$ cycloalkyl group; a $C_{6-20}$ aryl group; a $C_{4-20}$ heteroaryl group; or a $C_{6-20}$ aryl group having at least one substituent selected from the group consisting of a halogen atom, a $C_{1-10}$ halogenated alkyl group, —Si(R)(R')(R"), a $C_{1-10}$ alkyl group, a $C_{1-10}$ alkoxy group, a $C_{6-10}$ aryl group, a $C_{4-10}$ heteroaryl group and —N(R)(R'), and R, R' and R" are independently selected from the group consisting of a hydrogen atom, a $C_{1-10}$ alkyl group, a $C_{1-10}$ alkoxy group, a $C_{6-10}$ aryl group and a $C_{4-10}$ heteroaryl group.

6. The diphenyl anthracene derivative as claimed in claim 1, wherein the compound represented by formula 1 is at least one selected from the group consisting of compounds represented by formulas 1a through 1c:

<Formula 1a>
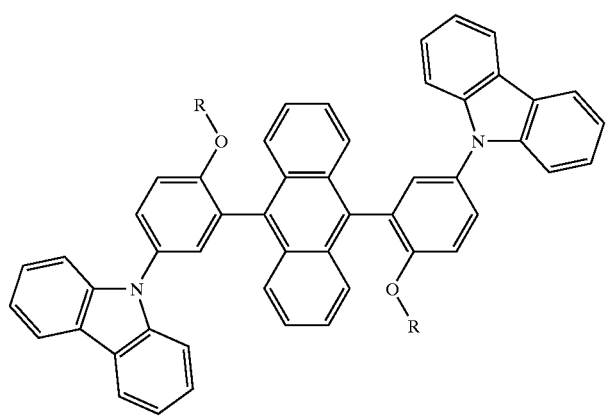

-continued

<Formula 1b>

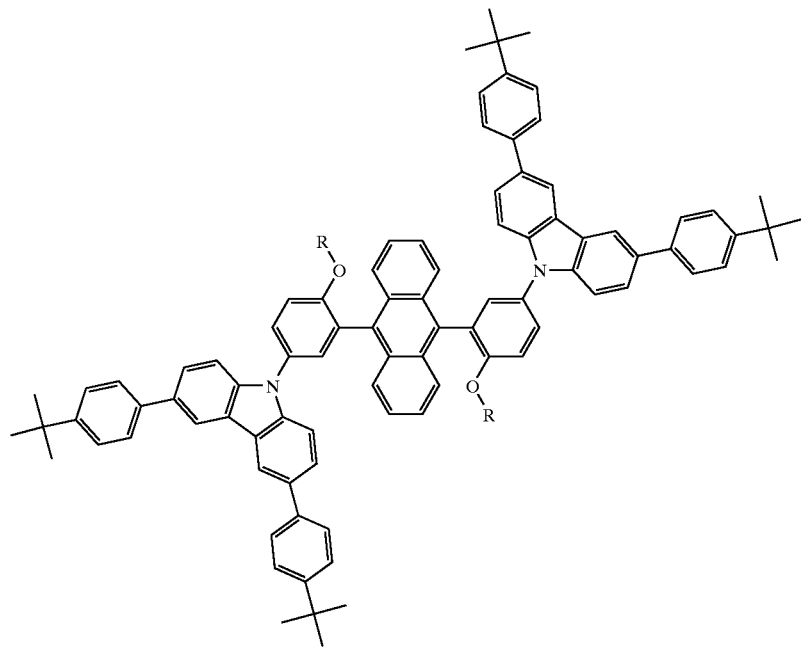

<Formula 1c>

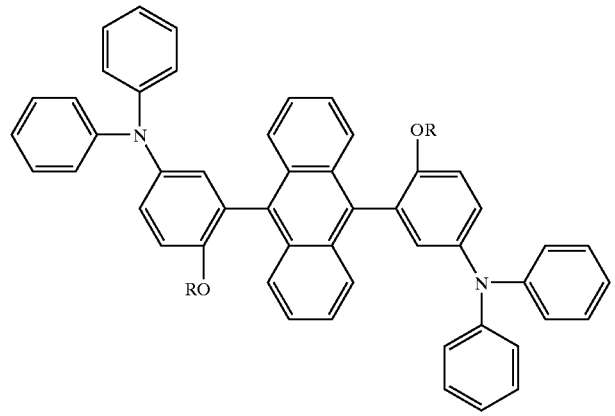

wherein R is a $C_{1-20}$ linear or branched alkyl group.

7. An organic EL device comprising an organic layer positioned between a pair of electrodes, the organic layer containing the diphenyl anthracene derivative as claimed in claim 1.

8. The organic EL device as claimed in claim 7, wherein the organic layer is an emissive layer, a hole injection layer or a hole transport layer.

9. The organic EL device as claimed in claim 7, wherein the organic layer is an emissive layer, and wherein the emissive layer comprises from about 0.1 to about 99.9% by weight of the diphenyl anthracene derivative and from about 99.9 to about 0.1% by weight of a light-emitting material.

10. The organic EL device as claimed in claim 9, wherein the light-emitting material is at least one selected from the group consisting of polyarylenes, poly(p-phenylenes), poly(p-phenylene vinylenes), and polyfluorenes.

* * * * *